(12) United States Patent
Michalak et al.

(10) Patent No.: US 7,321,061 B2
(45) Date of Patent: Jan. 22, 2008

(54) PROCESSES FOR THE PREPARATION OF ARYL- AND HETEROARYL-ALKYLSULFONYL HALIDES

(75) Inventors: Ronald S. Michalak, Congers, NY (US); Mousumi Ghosh, Elmwood Park, NJ (US); Mahmut Levent, Bloomfield, NJ (US)

(73) Assignee: Wyeth, Madison, NJ (US)

( * ) Notice: Subject to any disclaimer, the term of this patent is extended or adjusted under 35 U.S.C. 154(b) by 492 days.

(21) Appl. No.: 11/064,241

(22) Filed: Feb. 23, 2005

(65) Prior Publication Data
US 2005/0187408 A1 Aug. 25, 2005

Related U.S. Application Data

(60) Provisional application No. 60/547,600, filed on Feb. 25, 2004.

(51) Int. Cl.
*C07C 309/00* (2006.01)
(52) U.S. Cl. ..................................... 562/828
(58) Field of Classification Search ................ None
See application file for complete search history.

(56) References Cited

U.S. PATENT DOCUMENTS

| 2,199,568 | A | 5/1940 | Lange et al. |
| 2,507,408 | A | 5/1950 | Jacob |
| 2,888,486 | A | 5/1959 | Gregory |
| 2007/0021614 | A1 | 1/2007 | Michalak et al. |

FOREIGN PATENT DOCUMENTS

| DE | 48 722 | 8/1889 |
| DE | 150 313 | 3/1904 |
| WO | WO 03/048122 | 6/2003 |
| WO | WO 2007/013974 | 2/2007 |

OTHER PUBLICATIONS

Kirk-Othmer, *Kirk-Othmer Encyclopedia of Chemical Technology*, 5th Ed., available at www3.interscience.wiley.com/cgi-bin/mrwhome/104554789/home (last visited, May 9, 2005).
MARCH, *Advanced Organic Chemistry*, 4th ed., (New Jersey: John Wiley & Sons, 1992), p. 499.
Nakayama, et al., "Reaction of Arylmethanesulfonyl and Styrylmethanesulfonyl Chlorides with Triethylamine," *Tetrahedron Letters*, (1984) 25(40):4553-56.
Huang, et al., "Facile Synthesis of Sulfonyl Chlorides," *Tetrahedon Letters*, (1992) 33(19): 2657-60.
*Remington's Pharmaceutical Sciences*, 17th ed., (Easton, PA: Mack Publishing Company, 1985), p. 1418.
Khorana, H.G., "Carbodiimides: Part II. The Reaction of Sulphonic Acids with Carbodiimides. A New Method of Preparation of Sulphonic Anhydrides," *Canadian Journal of Chemistry*, (1953) 31: 585-88.
Field, L., "Aromatic Sulfonic Acid Anhydrides," *J. of the American Chem. Soc.*, (Jan. 1952) 74: 394-98.

Dmowski, W. and Piasecka-Maciejewska, K., "A Site Selective Functionalisation of 1,3-Bis(trifluoromethyl)benzene," *Tetrahedron*, (1998) 54:6781-92.
Leung et al., "The difluoromethylenesulfonic acid group as a monoanionic phosphate surrogate for obtaining PTP1B inhibitors," *Bioorganic & Medicinal Chemistry* (2002) 10(7):2309-2323.
Lichtenberger et al., "Sur les di-esters sulfoniques," *Bulletin de la Societe Chimique de France*, (1961) 363-371.
Abdellaoui et al., "Synthesis of the naphthalenic bioisostere of the anti-migraine drug sumatriptan," *Synthetic Communications* (1995) 25(9):1303-1311.
Freeman et al., "Intermediates in the peroxy acid oxidation of phenyl phenylmethanethiosulfinate[1,2]," *J Organic Chemistry* (1981) 46(20):3991-3996.
Hartman et al., "Synthesis and derivatization of novel 4-aroylthiophene-and furan-2-sulfonamides," *J Heterocyclic Chemistry* (1989) 26(6):1793-1798.
Rewcastle et al., "Potential antitumor agents. 63. Structure-activity relationships for side-chain analogues of the colon 38 active agent 9-oxo-9H-xanthene-4-acetic acid," *J Medicinal Chemistry* (1991) 34(9):2864-2870.
International Search Report dated Jun. 8, 2005 for International Application No. PCT/US2005/005624.
Abramovitch et al., "Solution and Flash Vacuum Pyrolysis of Some 2,6-Disubstituted α-Phenethylsulfonyl Azides and of α-Styrenesulfonyl Azide," *J. Org. Chem.*, 50:2066-2073 (1985).
Beilstein Registry No. 1747453, "ethanesulfonic acid methylamide, N-methyl-ethanesulfonamide," 1 page.
Beilstein Registry No. 2639938, "N-ethyl-cyclohexancsulfonamide," 1 page.
Beilstein Registry No. 2697078, "2-trifluoromethylbenzesulfonamide," 3 pages.
Beilstein Registry No. 2702138, "4-Amino-2-trifluoromethyl-benzolsulfonsaeure-(N-isopropyl-amid), " 2 pages.
Beilstein Registry No. 2703228, "4-Amino-2-trifluormethyl-benzosulfonsaeure-(N-butyl-amid)," 2 pages.
Beilstein Registry No. 2717732, "2-Cyclohexyl-aethan-sulfonamid," 1 page.
Beilstein Registry No. 3255360, "3-phenyl-propane-1-sulfonic acid amide," 1 page.
Beilstein Registry No. 5427164, "N-methyl 2-phenylethanesulfonamide," 1 page.
Brundish et al., "Design and Synthesis of Thrombin Inhibitors: Analogues of MD-805 with Reduced Stereogenicity and Improved Potency," *J. Med. Chem.*, 42:4584-4603 (1999).
"Herstellung aromatischer Sulfonsäurechloride," Houben-Weyl: Methoden der Organishen Chemie, 4th Edition, George Thieme Verlag, Stuttgart, Germany, p. 563 (1955).
International Search Report for PCT/US2006/028182, 6 pages (Jan. 24, 2007).
Written Opinion of the International Searching Authority for PCT/US2006/028182, 8 pages (Jan. 24, 2007).

*Primary Examiner*—Paul A. Zucker
(74) *Attorney, Agent, or Firm*—Fish & Richardson P.C.

(57) ABSTRACT

The present invention provides processes for the preparation of arylalkylsulfonyl halides and heteroarylalkylsufonyl halides of Formula I: Ar—R—$SO_2$—X, that are useful as intermediates in the preparation of pharmaceuticals.

29 Claims, No Drawings

PROCESSES FOR THE PREPARATION OF ARYL- AND HETEROARYL-ALKYLSULFONYL HALIDES

CROSS REFERENCE TO RELATED APPLICATIONS

This application claims priority benefit of U.S. Provisional Application Ser. No. 60/547,600 filed Feb. 25, 2004, which is incorporated by reference herein in its entirety.

FIELD OF THE INVENTION

The present invention relates to processes for the preparation of arylalkylsulfonyl halides and heteroarylalkylsulfonyl halides useful as intermediates in the preparation of, for example, pharmaceuticals.

BACKGROUND OF THE INVENTION

Sulfonyl chlorides are widely used in the chemical industry such as for the preparation of dyes, lithographic resists, and pharmaceuticals. They can be further transformed into other functional groups such as aromatic sulfones (by Friedel-Crafts sulfonylation of aromatic substrates) or sulfonamides (by reaction with amines) (see, e.g., *Kirk-Othmer Encyclopedia of Chemical Technology*). Sulfonamides are integral functional groups of a wide variety of therapeutic small molecule drugs such as antibacterial agents, diuretics, and cPLA$_2$ inhibitors.

A typical preparation of sulfonyl chlorides involves reaction of the sodium salt of a sulfonic acid with phosphorus pentachloride, sometimes in combination with phosphorus oxychloride or thionyl chloride, frequently with heating of the reaction mixture (see, e.g., March, *Advanced Organic Chemistry*, 4$^{th}$ ed., John Wiley & Sons, 1992, p. 499). These relatively harsh reaction conditions are unsuitable for the preparation of sterically hindered sulfonyl chlorides, such as arylalkylsulfonyl chlorides and the like, which can result in low yields due to the elimination of sulfur dioxide (Nakayama et al., *Tet Lett.*, 1984, 25, 4553-4556). A milder, infrequently used method for the synthesis of sulfonyl chlorides is the reaction of tetrabutylammonium salts of sulfonic acids with triphenylphosphine/sulfuryl chloride (Widlanski et al., *Tet Lett.*, 1992, 33, 2657-2660), a method that suffers from the disadvantage of poor atom efficiency.

Numerous sterically hindered sulfonyl halides such as (2,6-dimethylphenyl)-methanesulfonyl chloride and other aryl- and heteroaryl-sulfonyl halides are specifically useful in the preparation of cPLA$_2$ inhibitors for the treatment of asthma or arthritic and rheumatic disorders as described in, for example, WO 2003/048122. As discussed above, these intermediates can be difficult to prepare due to loss of sulfur dioxide at higher temperatures and formation of significant amounts of impurities. Thus, new and improved methods for making these compounds are needed, and the methods provided herein help meet these and other needs.

SUMMARY OF THE INVENTION

In some embodiments, the present invention provides processes for preparing a compound of Formula I:

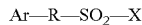    I wherein:

Ar is aryl or heteroaryl optionally substituted by one or more substituents, preferably up to five substituents, that are selected from the group consisting of halogen, $C_1$-$C_6$ alkyl, $C_3$-$C_7$ cycloalkyl, heterocycloalkyl, formyl, cyano, nitro, OH, $C_1$-$C_6$ alkoxy, arylalkyloxy, $C_1$-$C_6$ haloalkyl, $C_1$-$C_3$ perhaloalkyl, $C_1$-$C_6$ haloalkoxy, $C_1$-$C_3$ perhaloalkoxy, $NR^1R^2$, $NR^1COR^3$, aryl, aryloxy, heteroaryl and heteroaryloxy;

R is $C_1$-$C_6$ alkylenyl;

$R^1$ and $R^2$ are each, independently, H, $C_1$-$C_6$ alkyl or $C_3$-$C_7$ cycloalkyl; or $R^1$ and $R^2$ together with the N atom to which they are attached form a 5- or 6-membered heterocycle;

$R^3$ is H, $C_1$-$C_6$ alkyl or $C_3$-$C_7$ cycloalkyl; and

X is halogen;

comprising:

a) reacting a compound of Formula II:

Ar—R-L    II wherein L is a leaving group, with a Group I or II metal sulfite salt optionally in the presence of a phase transfer catalyst for a time and under conditions sufficient to form a sulfonic acid salt compound of Formula III:

    III wherein M is a Group I or II metal ion, where q is 1 where M is Group I metal ion, and q is 2 where M is a Group II metal ion;

b) reacting said compound of Formula III with a protic acid for a time and under conditions sufficient to form a sulfonic acid compound of Formula IV:

Ar—R—SO$_3$H    IV and c) reacting said compound of Formula IV with a halogen substitution reagent for a time and under conditions sufficient to form said compound of Formula I.

In some embodiments, the reacting of step a) is carried out in a solvent comprising water. In some embodiments, the reacting of step a) is carried out without the presence of a phase transfer catalyst. In further embodiments, the reacting of step a) is carried out in the presence of a phase transfer catalyst. In further embodiments, the reacting of step a) is carried out in a solvent comprising water and in the presence of a phase transfer catalyst In some embodiments, the compound of Formula III is isolated, preferably by precipitating the compound of Formula III and optionally filtering the resulting precipitate. In some embodiments, the precipitating of the compound of Formula III is induced by (1) addition of a water-soluble metal halide salt, which is preferably NaCl; (2) adding solvent that is not substantially miscible with water, which is preferably ethyl acetate; or both (1) and (2).

In some embodiments, protic acid of step (b) is an inorganic acid, which is preferably HCl, HBr, H$_3$PO$_4$, HNO$_3$, HClO$_4$, or H$_2$SO$_4$, or a combination thereof. In some more preferred embodiments, protic acid of step (b) is HCl. In some embodiments, the protic acid is gaseous HCl added to the reaction mixture or solvent containing the compound of Formula III.

In some embodiments, the reacting of step b) is carried out in a solvent comprising an alcohol, which preferably is methanol.

In some embodiments, the compound of Formula IV is isolated, preferably by precipitating the compound of Formula IV, and optionally filtering the resulting precipitate. In some embodiments, the compounds of Formula III and Formula IV are both isolated.

In some embodiments, the halogen substitution reagent is $SOCl_2$, $POCl_3$, $CCl_4$/triphenylphosphine, oxalyl chloride or oxalyl bromide, preferably oxalyl chloride.

In some embodiments, the reacting of step c) is carried out in the presence of an acyl transfer catalyst, which is preferably a tertiary amide, preferably N,N-dimethylformamide.

In further embodiments, the invention provides processes for preparing a compound of Formula IV:

Ar—R—SO$_3$H      IV wherein:

Ar and R are as defined above; comprising:

a) reacting in a solvent a compound of Formula II:

Ar—R-L      II wherein L is as defined above, with a Group I or II metal sulfite salt optionally in the presence of a phase transfer catalyst for a time and under conditions sufficient to form a sulfonic acid salt compound of Formula III:

(Ar—R—SO$_3^{-1}$)$_q$M      III wherein M and q are as defined above; and b) reacting said compound of Formula III with a protic acid for a time and under conditions sufficient to form said compound of Formula IV.

In some embodiments, the compound of Formula III is isolated by precipitating the compound of Formula III optionally followed by filtering. In some preferred embodiments, the precipitating is facilitated by (1) treating the reaction mixture of step (a) with a water-soluble metal halide salt which is preferably NaCl; or (2) adding to the reaction mixture of step (a) solvent that is not substantially miscible with water, which is preferably ethyl acetate; or by both (1) and (2). In some embodiments, the reacting of step (a) is carried out in a solvent comprising water. In further embodiments, the reacting of step (a) is carried out in the presence of a phase transfer catalyst. In further preferred embodiments, the reacting of step (b) is carried out in a solvent comprising an alcohol, which is preferably methanol. In some preferred embodiments, the protic acid of step (b) is HCl, preferably gaseous HCl added to the solvent containing the compound of Formula III.

In further embodiments, the present invention provides processes for preparing a compound of Formula III:

(Ar—R—SO$_3^{-1}$)$_q$M      III wherein M is a Group I or II metal ion, where q is 1 where M is Group I metal ion, and q is 2 where M is a Group II metal ion;

Ar is aryl or heteroaryl optionally substituted by one or more substituents, preferably up to five substituents, that are selected from the group consisting of halogen, $C_1$-$C_6$ alkyl, $C_3$-$C_7$ cycloalkyl, heterocycloalkyl, formyl, cyano, nitro, OH, $C_1$-$C_6$ alkoxy, arylalkyloxy, $C_1$-$C_6$ haloalkyl, $C_1$-$C_3$ perhaloalkyl, $C_1$-$C_6$ haloalkoxy, $C_1$-$C_3$ perhaloalkoxy, $NR^1R^2$, $NR^1COR^3$, aryl, aryloxy, heteroaryl and heteroaryloxy;

R is $C_1$-$C_6$ alkylenyl;

$R^1$ and $R^2$ are each, independently selected from the group consisting of H, $C_1$-$C_6$ alkyl and $C_3$-$C_7$ cycloalkyl; or $R^1$ and $R^2$ together with the N atom to which they are attached form a 5- or 6-membered heterocycle; and $R^3$ is selected from the group consisting of H, $C_1$-$C_6$ alkyl and $C_3$-$C_7$ cycloalkyl;

comprising:

reacting a compound of Formula II:

Ar—R-L      II wherein L is a leaving group, with a Group I or II metal sulfite salt optionally in the presence of a phase transfer catalyst for a time and under conditions sufficient to form a reaction mixture containing said compound of Formula III; and isolating said compound of Formula III by precipitating the compound of Formula III from the reaction mixture. In some embodiments, the precipitation is facilitated by (1) treating the reaction mixture with a water-soluble metal halide salt which is preferably NaCl; or (2) adding to the reaction mixture solvent that is not substantially miscible with water, that is preferably ethyl acetate; or both (1) and (2). In some embodiments, the reacting is carried out in a solvent comprising water, preferably in the presence of a phase transfer catalyst.

In some embodiments of each of the foregoing processes, the water soluble metal halide salt is NaCl. In further embodiments of each of the foregoing processes, the phase transfer catalyst is tetrabutyl ammonium iodide. In further embodiments of each of the foregoing processes, the compound of formula II, for example 2,6-dimethyl benzyl chloride or 2,6-dimethyl benzyl bromide, is reacted with $Na_2SO_3$. In further embodiments of some of the foregoing processes, the alcohol solvent to which the protic acid is added is methanol. In further embodiments of some of the foregoing processes, the protic inorganic acid is gaseous HCl. In further embodiments, the compound of Formula IV is isolated via evaporation of the alcohol solvent.

In some embodiments of the foregoing processes, the reacting of the sulfonic acid species of Formula IV, for example 2,6-dimethylbenzyl sulfonic acid, with the halogen substitution reagent, for example oxalyl chloride, is carried out at less than about −10° C. for the duration of the oxalyl chloride addition. Suitable solvents for this reaction include, for example, an ether (e.g., tetrahydrofuran) or a mixture of ethers.

In some embodiments of the foregoing processes, Ar is phenyl optionally substituted by one or more substituents independently selected from halogen, $C_1$-$C_6$ alkyl, $C_3$-$C_7$ cycloalkyl, heterocycloalkyl, cyano, nitro, OH, $C_1$-$C_6$ alkoxy, $C_1$-$C_6$ haloalkyl, $C_1$-$C_6$ haloalkoxy, $NR^1R^2$, $NR^1COR^3$, aryl and heteroaryl, preferably the substituents are independently selected from $C_1$-$C_6$ alkyl, $C_1$-$C_6$ alkoxy, halogen, CN, $NO_2$, $NR^1R^2$ and $NR^1COR^3$. In some preferred embodiments, Ar is phenyl substituted by one or more halogen, $C_1$-$C_6$ alkyl, $C_1$-$C_3$ perhaloalkyl, formyl, or arylalkyloxy substituent. In some embodiments, Ar is phenyl substituted with at least one substituent at the 2 position or the 6 position; or substituents at both the 2 position and the 6 position. In other embodiments, Ar is phenyl substituted at the 3 position and the 4 position, such as, for example, 3,4-dichloro phenyl. In some further embodiments of the foregoing processes, R is $C_1$-$C_4$ alkylene, or $C_1$-$C_6$ straight-chained alkylene, preferably methylene or ethylene, more preferably methylene.

In some embodiments of the foregoing processes, L is independently halogen, $OSO_2CH_3$, $OSO_2CF_3$ or $OSO_2$-aryl' wherein aryl' is a phenyl group optionally substituted with 1, 2 or 3 substituents independently selected from $C_1$-$C_3$ alkyl and halogen. Preferably, L is Cl.

In some embodiments of the foregoing processes, M is Na+ ion or K+ ion, preferably Na+ ion.

In some preferred embodiments of the foregoing processes, X is Cl.

In some further preferred embodiments of the foregoing processes, Ar is phenyl optionally substituted by one or more substituent selected from halogen, $C_1$-$C_6$ alkyl, $C_1$-$C_3$ perhaloalkyl, formyl, arylalkyloxy, $NR^1R^2$ and $NR^1COR^3$; R is methylene or ethylene; $R^1$ and $R^2$ are each, independently, H or $C_1$-$C_6$ alkyl; $R^3$ is H or $C_1$-$C_6$ alkyl; X is Cl; L is halogen; the metal sulfite salt of step (a) is $Na_2SO_3$; the phase transfer catalyst of step (a) is present; the sulfonic acid salt compound of Formula III has the Formula $NaSO_3$—R—Ar; step (a) further comprises isolating the compound of Formula III step (b) further comprises isolating the compound of Formula IV; and the halogen substitution reagent of step (c) is oxalyl chloride.

In other preferred embodiments of the processes of the present invention, step (a) is carried out without the presence of a phase transfer catalyst. In some such embodiments, the Ar—R-L of Formula II is 2,3-dichlorobenzyl chloride and the compound of Formula I is (2,3-dichlorophenyl)-methanesulfonyl chloride.

In other preferred embodiments, the processes of the present invention are used to prepare (3,4-dichlorophenyl)-methanesulfonyl chloride, (2,6-dimethylpheny)-methanesulfonyl chloride, (2-methylphenyl)-methanesulfonyl chloride, (2,6-difluorophenyl)-methanesulfonyl chloride, 2-fluoro-6-(trifluoromethylphenyl)-methanesulfonyl chloride, 2,6-Bis(trifluoromethylphenyl)-methanesulfonyl chloride, (2-trifluoromethylphenyl)-methanesulfonyl chloride, (2-Benzyloxyphenyl)-methanesulfonyl chloride, (2,3-dichlorophenyl)-methanesulfonyl chloride or (2-formylphenyl)-methanesulfonyl chloride.

DETAILED DESCRIPTION OF EMBODIMENTS OF THE INVENTION

The present invention provides a process for the preparation of aryl- and heteroaryl-alkylsulfonyl halides including (2,6-dimethyl-phenyl)-methanesulfonyl chloride, an intermediate in the synthesis of certain $cPLA_2$ inhibitors. In some embodiments, the methods generally involve the formation of sulfonic acid prior to conversion to the sulfonyl halide.

A general outline of some embodiments of the processes of the present invention is provided in Scheme I, where constituent members of the depicted compounds of Formulas I, II, III, and IV are defined hereinabove.

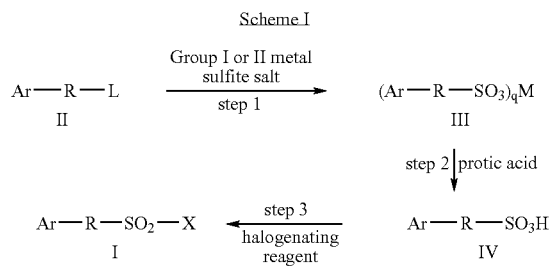

Scheme I

As shown in Scheme I, sulfonic acids of Formula IV can be converted to sulfonyl halides by reaction with a halogen substitution reagent. Halogen substitution reagents, as used herein, are reagents that can convert a non-halogen substituent (such as, for example, H or OH) to a halogen substituent. Halogen substitution reagents of the present invention can, for example, convert a sulfonic acid moiety to a sulfonyl halide moiety. Numerous reagents capable of carrying out this conversion are known in the art. Some preferred halogen substitution reagents include $SOCl_2$, $POCl_3$, $CCl_4$/triphenylphosphine, oxalyl chloride or oxalyl bromide. In some more preferred embodiments, the halogen substitution reagent is oxalyl chloride. The halogen substitution agent is preferably used in excess quantity, particularly if there is residual solvent in either the starting material, solvents or both. When oxalyl chloride is used as the halogen substitution agent, it can be used in a range from about 1 to about 6 equivalents; about 2 to about 4 equivalents or about 3 to about 3.5 equivalents with respect to the amount of sulfonic acid reagent (compound of Formula IV). One skilled in the art will recognize that the amount of halogen substitution agent used will depend, inter alia, on the amount of water in the starting material or solvent and the nature and reactivity of the starting material and solvents.

Suitable solvents for the halogen substitution reaction (e.g., step 3 of Scheme I) include any organic solvent that can at least partially dissolve the compound of Formula IV. Preferred solvents include non-polar or weakly polar solvents, including acetonitrile, aromatic hydrocarbons such as benzene and toluene, and halogenated solvents such as 1,2-dichloroethane and methylene chloride. More preferred solvents are ethers. Suitable ethers include tetrahydrofuran, dioxane, diethyl ether, dibutyl ether, diisopropyl ether or mixtures thereof and the like. A more preferred ether is tetrahydrofuran.

The halogen substitution reaction can be carried out at any suitable temperature. For example, in some preferred embodiments, the reaction can be carried out at about −40° C. to about room temperature. In some more preferred embodiments, the reaction can be carried out below about −10° C.

The sulfonyl halide-forming step (e.g., step 3 of Scheme I) of processes of the invention can also be carried out in the presence of an acyl transfer catalyst, such as a tertiary amide (e.g., dimethylformamide). The acyl transfer catalyst can be provided in an amount sufficient to accelerate the reaction rate. In preferred embodiments, the acyl transfer catalyst is present in less than about one equivalent relative to the amount of sulfonic acid reagent. In more preferred embodiments, the acyl transfer catalyst is present in an amount of about 0.01 to about 0.5 equivalents; even more preferred, about 0.1 to about 0.2 equivalents, relative to the amount of sulfonic acid reagent.

The compounds of Formula I can be isolated from the reaction mixture by precipitation and filtration. Any of numerous well known methods for inducing precipitation can be used. In some preferred embodiments, an anti-solvent such as water or a solvent containing water can be added to the reaction mixture to induce precipitation. It has been observed that use of water as an anti-solvent can reduce decomposition rate of the sulfonyl halide product relative to the decomposition rate observed when an organic solvent such as heptane is used, resulting in improved yields. In some more preferred embodiments, precipitation can be facilitated by lowering the temperature of the reaction mixture to, for example, to below about −20° C.

As shown in Scheme I, sulfonic acids of Formula IV can be prepared by reacting sulfonic acid salts (sulfonate salts) of Formula III with a protic acid. Suitable protic acids are of sufficient strength so as to be capable of converting a sulfonate salt to its corresponding acid according to the processes of the invention. For example, the protic acid can be a strong inorganic acid such as HCl, HBr, $H_3PO_4$, $HNO_3$, $HClO_4$, $H_2SO_4$, and the like. In other embodiments, the protic acid can be an organic acid. Example organic acids include formic methanesulfonic acid, p-toluene sulfonic acid, benzenesulfonic acid, trifluoroacetic acid and other strong organic acids. In some embodiments, the protic acid is provided in gaseous form. In some preferred embodiments, the inorganic acid is HCl. In some more preferred embodiments, the inorganic acid is gaseous HCl that is added to the reaction solvent containing the sulfonate salt. In a preferred embodiment, the protic acid is provided in excess molar equivalents relative to the sulfonic acid salt of Formula III.

Formation of the sulfonic acid compound of Formula IV can be carried out in any suitable solvent. For example, organic solvents in which the compound of Formula III is at least partially soluble are suitable. In some preferred embodiments, the solvent poorly dissolves metal halide salts, such as NaCl or KCl, thereby thermodynamically driving the reaction by precipitation of metal halide salt. In further preferred embodiments, the solvent can contain an alcohol, such as methanol, ethanol, isopropanol, and the like, or a mixture thereof. The solvent can also contain water. In yet more preferred embodiments, the solvent contains methanol. Reaction temperature can be readily determined by the skilled artisan. For example, the reaction can be carried out at a temperature below room temperature, such as about −20 to about 10° C. In some preferred embodiments, the reaction is carried out at about 0 or below about 10° C.

The sulfonic acid compound of Formula IV can be isolated according to routine methods. Isolation can be carried out, for example, by precipitating the product from the reaction mixture. Precipitation can be induced by any suitable means. In some preferred embodiments, precipitation can be induced by any of, or a combination of, concentrating the reaction mixture (optionally azeotroped), cooling (e.g., to less than about 10° C.), and adding of non-polar organic solvent such as an alkane (e.g., heptane, hexane, pentane, etc.).

The present invention also provides a process for preparing a sulfonic acid salt (sulfonate salt) compound of Formula III by reacting a compound of Formula II: Ar—R-L (wherein Ar, R and L are defined hereinabove) with a Group I or II metal sulfite salt optionally in the presence of a phase transfer catalyst as shown in step 1 of scheme 1 above. Any Group I or II metal sulfite salt is suitable, for example, and without limitation, $Li_2SO_3$, $Na_2SO_3$, $K_2SO_3$, $MgSO_3$, $CaSO_3$, and the like. Group I or II metal sulfite salts can be provided in molar excess of, for example, about 2 eq, to about 1 eq, relative to the amount of compound of Formula II. In some preferred embodiments, the metal salt is $Na_2SO_3$ or $K_2SO_3$, more preferably $Na_2SO_3$.

In a preferred embodiment, the formation of the sulfonate salt compounds of Formula III can be carried out in the presence of a phase transfer catalyst. In some preferred embodiments, the phase transfer catalyst is a quaternary ammonium halide, preferably tetrabutyl ammonium iodide. The phase transfer catalyst can be provided in an amount suitable to accelerate the reaction rate. In some preferred embodiments, the phase transfer catalyst is present in about 0.1 to 2% or more preferably 0.5 to 1% by weight.

Any suitable solvent can be employed, such as solvent that can at least partially dissolve Group I or II metal sulfite salts. In some embodiments, the solvent contains water. In some preferred embodiments, the solvent contains more than about 50%, more preferably about 75%, even more preferably more than about 90%, still more preferably more than about 95%, and yet more preferably more than about 99% water. The reaction can also be carried out at any suitable temperature. In some preferred embodiments, the temperature is elevated. In still further preferred embodiments, the reaction is carried out at about 100° C.

Isolation of the compound of Formula III from the reaction mixture can be carried out by any routine method. In some embodiments, the compound of Formula III is precipitated from the reaction mixture. In some preferred embodiments, the precipitation is facilitated by, for example, treatment of the reaction mixture with a water-soluble inorganic salt. While not wishing to be bound by any particular theory, it is believed the addition of a sufficient amount of water-soluble inorganic salt thermodynamically drives the compound of Formula III out of solution, thereby facilitating isolation and purification. In some preferred embodiments, the water-soluble inorganic salt is NaCl or KCl, more preferably NaCl. In further embodiments, isolation of the compound of Formula III can be further facilitated by the addition to the reaction mixture of an organic solvent that is not substantially miscible with water. Examples of suitable solvents include ethyl acetate, ethers (e.g. ethyl ether and the like), alkanes (e.g., hexanes, petroleum ether, etc.), aromatics (e.g., benzene, toluene, xylene, etc.), and the like, with ethyl acetate being most preferred. While again not wishing to be bound by a particular theory, it is believed that the addition of organic solvent aids in maintaining impurities in solution when precipitating the compound of Formula III. In some preferred embodiments, the reaction mixture can also be cooled (e.g., less than about 10° C.) to help induce precipitation.

Numerous advantages of the present invention are apparent to the art-skilled. For example, preparation of the sulfonic acid intermediate prior to sulfonyl halide formation allows for improved yields by avoiding sulfur dioxide loss typically observed in the preparation of sterically hindered sulfonyl halides. Additionally, the preparation and isolation methods described herein help maximize yields.

In some embodiments of the invention, multi-step processes are carried out stepwise and each intermediate is isolated before proceeding to the next step. In other embodiments of the invention, some of the intermediates are isolated and others are not. In yet other embodiments, none of the intermediates are completely isolated and all of the reactions take place in a single reactor vessel.

It is understood in the generic description above and for other groups described herein that, in each instance any variable group may be independently substituted by their allowed groups. Thus, for example, where a structure is described wherein two $R_2$ groups are simultaneously present on the same compound; the two $R_2$ groups can represent different groups.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "alkyl", employed alone, is defined herein as, unless otherwise stated, either a straight-chain or branched saturated hydrocarbon moiety. In some embodiments, the alkyl moiety contains 1 to 12, 1 to 10, 1 to 8, 1 to 6, or 1 to 4 carbon atoms. Examples of saturated hydrocarbon alkyl moieties include, but are not limited to, chemical groups such as methyl, ethyl, n-propyl, isopropyl, n-butyl, tertbutyl, isobutyl, sec-butyl; higher homologs such as n-pentyl, n-hexyl, n-heptyl, n-octyl, and the like.

The term "alkylenyl" refers to a bivalent straight-chained or branched alkyl group.

As used herein, "haloalkyl" refers to an alkyl group having one or more halogen substituents, up to and including perhalogenated species. Thus, examples of haloalkyl groups include perhaloalkyl groups such as $CF_3$, $C_2F_5$, $CCl_3$, $C_2Cl_5$, and the like, as well as groups having less than perhalo substitution, such as $CHF_2$, $CHCl_2$ and the like. The term "perhaloalkyl" is intended to denote an alkyl group in which all of the hydrogen atoms are replaced with halogen atoms.

The term "alkoxy", employed alone or in combination with other terms, is defined herein as, unless otherwise stated, —O-alkyl. Examples of alkoxy moieties include, but are not limited to, chemical groups such as methoxy, ethoxy, isopropoxy, sec-butoxy, tert-butoxy, and homologs, isomers, and the like.

The term "haloalkoxy", employed alone or in combination with other terms, is defined herein as, unless otherwise stated, —O-haloalkyl. Examples of haloalkoxy moieties include, but are not limited to, chemical groups such —$OCF_3$, and the like.

The term "cycloalkyl", employed alone or in combination with other terms, is defined herein as, unless otherwise stated, a monocyclic, bicyclic, tricyclic, fused, bridged, or spiro monovalent non-aromatic hydrocarbon moiety of 3-8 or 3-7 carbon atoms. Also included in the definition of cycloalkyl are moieties that have one or more aromatic rings fused (i.e., having a bond in common with) to the nonaromatic ring. Any suitable ring position of the cycloalkyl moiety can be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, and the like.

As used herein, "heterocycloalkyl" refers to a cycloalkyl group (e.g. of 3-12 atoms) wherein one or more (e.g., up to 4 atoms) are replaced by a heteroatom such as an O, S, N or P atom. Also included in the definition of heterocycloalkyl are moieties that have one or more (e.g., two) aromatic rings fused (i.e., having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups. In some embodiments, heterocycloalkyl is a 3-12 membered group having 1-4 heteroatoms the same or different selected from oxygen, nitrogen and sulfur, having one or two benzene rings fused thereto, said group being bonded via a ring carbon or a nitrogen atom.

The terms "halo" or "halogen", employed alone or in combination with other terms, is defined herein as, unless otherwise stated, fluoro, chloro, bromo, or iodo.

The term "aryl", employed alone or in combination with other terms, is defined herein as, unless otherwise stated, an aromatic hydrocarbon of up to 14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like.

The term "aryloxy" as used herein means a group of formula —O-aryl, where the term "aryl" has the definition as previously described herein.

The term "arylalkyl" or "aralkyl," employed alone or in combination with other terms, is defined herein as, unless otherwise stated, an alkyl, as herein before defined, substituted with an aryl moiety as defined herein. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "arylalkyloxy" as used herein means a group of formula —O-arylalkyl, where the term "arylalkyl" has the definition as previously described herein.

As used herein, "heteroaryl" groups are monocyclic and polycyclic (e.g., three rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms. In some embodiments, heteroaryl is an aromatic 5-24 membered mono- or poly- (e.g., di- or tri-) cyclic group having 1-4 heteroatoms the same or different selected from oxygen, nitrogen and sulfur.

As used herein, "heterocycle" refers to a heteroaryl or heterocycloalkyl group.

The term "heteroaryloxy" as used herein means a group of formula —O-heteroaryl, where the term "heteroaryl" has the definition as previously described herein.

As used herein, the term "leaving group" refers to a moiety that can be displaced by another moiety, such as by nucleophilic attack, during a chemical reaction. Leaving groups are well known in the art and include, for example, halides and $OSO_2$—R' where R' is, for example, alkyl, haloalkyl, or aryl optionally substituted by halo, alkyl, alkoxy, amino, and the like. Some example leaving groups include chloro, bromo, iodo, mesylate, tosylate, and other similar groups.

As used herein, the term "reacting" refers to the bringing together of designated chemical reactants such that a chemical transformation takes place generating a compound different from any initially introduced into the system. Reacting can take place in the presence or absence of solvent.

As used herein, the term "precipitating" is used as known in the art and generally refers to the formation of solid (e.g., precipitate) from a solution in which the solid is dissolved. The solid can be amorphous or crystalline. Methods of precipitation are well known in the art and include, for example, increasing the proportion of solvent in which a solute is insoluble, decreasing temperature, chemically transforming the solute such that it becomes no longer soluble in its solvent, and the like.

The compounds of the present invention can contain an asymmetric atom, and some of the compounds can contain one or more asymmetric atoms or centers, which can thus give rise to optical isomers (enantiomers) and diastereomers.

The present invention includes such optical isomers (enantiomers) and diastereomers (geometric isomers), as well as, the racemic and resolved, enantiomerically pure R and S stereoisomers, as well as, other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds provided herein can also include their salts formed from, for example, mineral or organic acid salts of basic residues such as amines; alkali or organic salts of acidic residues such as carboxylic acids; and the like. The invention includes acceptable salt forms formed from the addition reaction with either inorganic or organic acids. Additionally, this invention includes quaternary ammonium salts of the compounds herein, which can be prepared by reacting the nucleophilic amines with a suitably reactive alkylating agent such as an alkyl halide or benzyl halide. Lists of suitable salts are found in *Remington's Pharmaceutical Sciences*, 17th ed., Mack Publishing Company, Easton, Pa., 1985, p. 1418, the disclosure of which is hereby incorporated by reference.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as ketoenol tautomers. Tautomeric forms can be in equilibrium or sterically locked into one form by appropriate substitution.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas. Some example solvents suitable for the processes described herein include halogenated hydrocarbons (e.g., methylene chloride), aromatic hydrocarbons (e.g., benzene, toluene, etc.), and ethers (e.g., diethyl ether, tetrahydrofuran, etc.).

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions are typically carried out at reduced temperatures); and the kinetics of the reaction (e.g., a high activation energy barrier typically necessitates elevated temperatures). "Elevated temperature" refers to temperatures above room temperature (about 20° C.) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments of the processes described herein, the following exemplified compounds can be made from their respective preparation materials as shown in Table 1, and in the Examples, below.

TABLE 1

| Ar | R | X | Compound of Formula I |
|---|---|---|---|
| 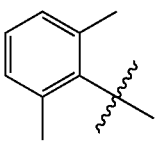 | 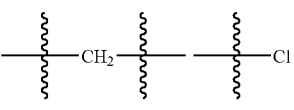 —CH$_2$— | 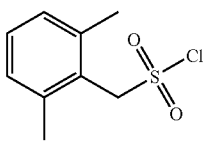 —Cl | 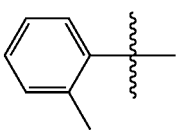 |
| 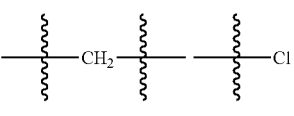 | 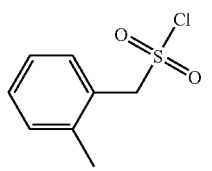 —CH$_2$— | —Cl | |

TABLE 1-continued
| Ar | R | X | Compound of Formula I |
|---|---|---|---|
| 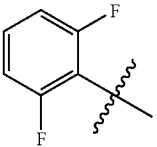 | 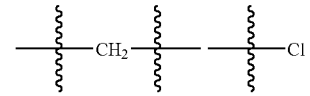 —CH$_2$— | 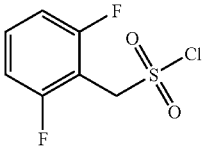 —Cl | 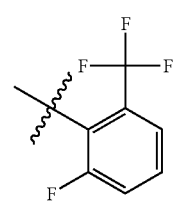 |
| 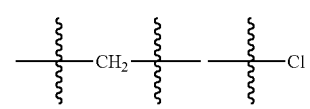 | 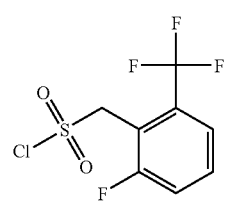 —CH$_2$— | —Cl | 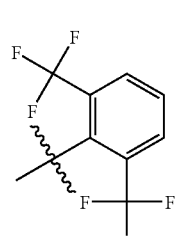 |
| 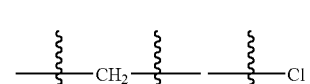 | 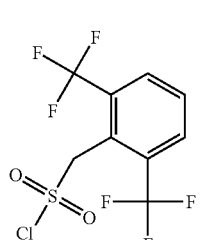 —CH$_2$— | —Cl | 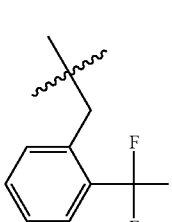 |
| 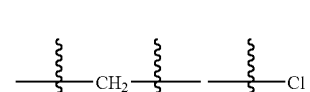 | 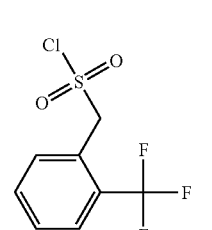 —CH$_2$— | —Cl | 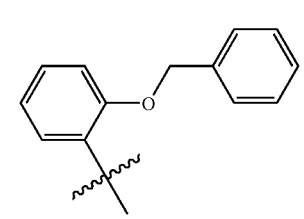 |
| 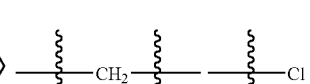 | 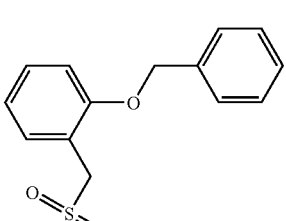 —CH$_2$— | —Cl | 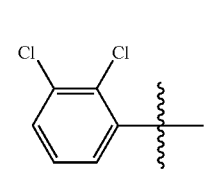 |
| 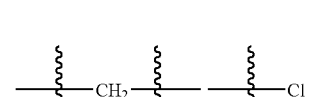 | 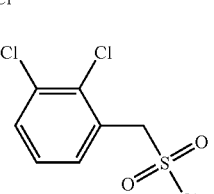 —CH$_2$— | —Cl | 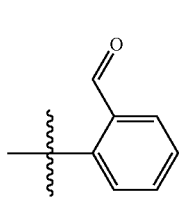 |
| 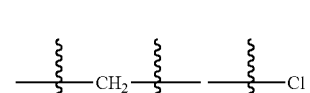 | —CH$_2$— | —Cl | 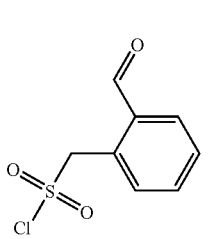 |

TABLE 1-continued

| Ar | R | X | Compound of Formula I |
|---|---|---|---|
| 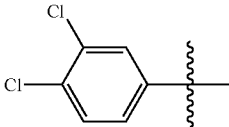 | 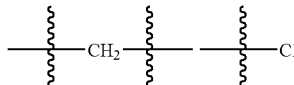 |  | 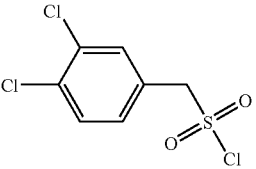 |

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

PREPARATION OF (2,6-DIMETHYL-PHENYL)-METHANESULFONYL CHLORIDE

Step 1: Preparation of (2,6-Dimethyl-phenyl)-methanesulfonic acid sodium salt

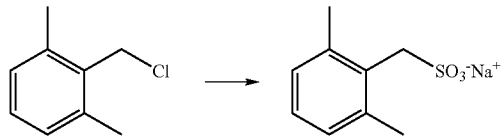

Sodium sulfite (442.4 g) was added to a stirred mixture of 2-chloromethyl-1,3-dimethyl-benzene (526.6 g), tetrabutylammonium iodide (6.4 g) and water (3.0 L). The mixture was warmed to reflux for 1 h. As the mixture cooled to room temperature, sodium chloride (526 g) and ethyl acetate (1.4 l) were added. The mixture was stirred and cooled to <10° C. The product was collected by filtration and washed with ethyl acetate (250 mL) and acetone (500 mL). The product was dried in vacuo at 60° C. to constant weight to give (2,6-dimethyl-phenyl)-methanesulfonic acid sodium salt (634 g, 88%). $^1$H NMR (300 MHz, DMSO$_{d6}$): δ 7.17-6.91 (m, 3H, ArH), 3.96 (s, 2H, CH$_2$), and 2.29 (s, 6H, CH$_3$).

Step 2: Preparation of (2,6-Dimethyl-phenyl)-methanesulfonic acid

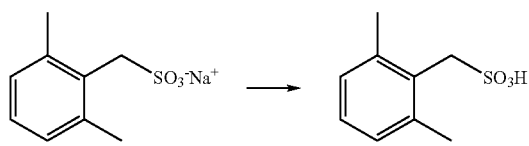

Methanol (2.2 L) and (2,6-dimethyl-phenyl)-methanesulfonic acid sodium salt (185 g) were combined in a multi-necked 5 L flask equipped with overhead stirring. The mixture was cooled to 0° C. and hydrogen chloride (112 g) was passed through the mixture, maintaining an internal temperature of <10° C. The mixture was stirred for 2 h and allowed to warm to room temperature. The mixture was clarified by filtration. The filtrate was concentrated to 600 mL volume at ambient pressure and azeotroped with toluene (3×600 mL). Heptane (1.1 L) was added to the mixture as it cooled to <10° C. The solid product was collected by filtration and washed with heptane (100 mL). The product was dried at 40° C. in vacuo to constant weight to give (2,6-dimethyl-phenyl)-methanesulfonic acid (149 g, 89%). $^1$H NMR (300 MHz, DMSO$_{d6}$): δ 7.0-6.91 (m, 3H, ArH), 4.40 (s, 2H, CH$_2$), and 2.34 (s, 6H, CH$_3$).

Step 3: Preparation of (2,6-Dimethyl-phenyl)-methanesulfonyl chloride

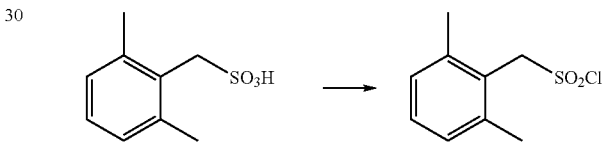

Tetrahydrofuran (3.0 L), (2,6-dimethyl-phenyl)-methanesulfonic acid (300 g, containing 12% water by KF analysis, or 266 g corrected for water content), and N,N-dimethylformamide (15 g) were combined in a 5 L multi-necked flask equipped with overhead stirring. The reaction mixture was cooled to −20° C. and oxalyl chloride (655.5 g) was added slowly over 1 h. The reaction mixture was clarified by filtration and concentrated to a volume of 1 L. The filtrate was transferred to a flask equipped with overhead stirring and cooled to −40° C. Water (900 mL) was added over 30 minutes, maintaining an internal temperature of <−10° C. The product was collected by filtration, washed with water and heptane, and dried to give (2,6-dimethyl-phenyl)-methanesulfonyl chloride (277 g, 96%). $^1$H NMR (300 MHz, CDCl$_3$): δ 7.25-7.04 (m, 3H, ArH), 5.17 (s, CH$_2$), and 2.50 (s, 6H, CH$_3$).

Example 2

PREPARATION OF (2-METHYLPHENYL)-METHANESULFONYL CHLORIDE

Step 1: Preparation of (2-Methylphenyl)-methanesulfonic acid sodium salt

Using the procedure described in Example 1, Step 1, α-bromo-o-xylene (100 g, 0.54 mol) afforded (2-methylphenyl)-methanesulfonic acid sodium salt (75 g, 66%), a white solid. LC-MS showed the molecular ion of the sulfonic acid. (G8382-72, G8382-49)

Step 2: Preparation of (2-Methylphenyl)-methanesulfonic acid

Using the procedure described in Example 1, Step 2, (2-methylphenyl)-methanesulfonic acid sodium salt (12 g, 58 mmol) afforded (2-methylphenyl)-methanesulfonic acid (10.6 g, ~100%), a pale yellow solid. (L25213-78)

Step 3: Preparation of (2-Methylphenyl)-methanesulfonyl chloride

Using the procedure described in Example 1, Step 3, (2-methylphenyl)-methanesulfonic acid (10.6 g, 57 mmol) afforded (2-methylphenyl)-methanesulfonyl chloride (11.8 g, 100%). $^1$HNMR (400 MHz, CDCl$_3$) δ 2.48 (s, 3 H), 4.97 (s, 2 H), 7.3 (d, J=7.3 Hz, 2 H), 7.33-7.41 (m, 1 H), 7.45 (d, J=7.6 Hz, 1 H). (L25213-80)

Example 3

PREPARATION OF (2,6-DIFLUOROPHENYL)-METHANESULFONYL CHLORIDE

Step 1: Preparation of (2,6-Difluorophenyl)-methanesulfonic acid sodium salt

Using the procedure described in Example 1, Step 1, 2,6-Difluorobenzyl bromide (50 g, 0.24 mol) afforded (2,6-difluorophenyl)-methanesulfonic acid sodium salt (38.9 g, 70%), a white solid. (G8324-105)

Step 2: Preparation of (2,6-Difluorophenyl)-methanesulfonic acid

Using the procedure described in Example 1, Step 2, (2,6-difluorophenyl)-methanesulfonic sodium salt (10 g, 44 mmol) afforded (2,6-difluorophenyl)-methanesulfonic acid (9.5 g), a viscous orange oil, which was used without purification. (L26913-131)

Step 3 Preparation of (2,6-Difluorophenyl)-methanesulfonyl chloride

Using the procedure described in Example 1, Step 3, (2,6-difluorophenyl)-methanesulfonic acid (9.5 g, 44 mmol) afforded (2,6-difluorophenyl)-methanesulfonyl chloride (1.3 g, 14%). $^1$HNMR (400 MHz, CDCl$_3$) δ 5.02 (s, 2 H), 7.00-7.11 (m, 2 H), 7.40-7.57 (m, 1 H). (L26913-136)

Example 4

PREPARATION OF 2-FLUORO-6-(TRIFLUOROMETHYLPHENYL)-METHANESULFONYL CHLORIDE

Step 1: Preparation of 2-Fluoro-6-(trifluoromethylphenyl)-methanesulfonic acid sodium salt Using the procedure described in Example 1, Step 1, 2-fluoro-6-(trifluoromethylphenyl)benzyl bromide (15 g, 61 mmol) afforded 2-fluoro-6-(trifluoromethylphenyl)-methanesulfonic acid sodium salt (15 g, 89%), a white solid. $^1$HNMR (400 MHz, DMSO-d$_6$) δ 4.02 (s, 2 H), 7.26-7.66 (m, 3 H). (L26913-185)

Step 2: Preparation of 2-Fluoro-6-(trifluoromethylphenyl)-methanesulfonic acid

Using the procedure described in Example 1, Step 2, 2-fluoro-6-(trifluoromethylphenyl)-methanesulfonic acid sodium salt (15 g, 53 mmol) afforded 2-fluoro-6-(trifluoromethylphenyl)-methanesulfonic acid (15 g), a pale orange oil, which was used without further purification. $^1$HNMR (400 MHz, DMSO-d$_6$) δ 4.12 (s, 2 H), 7.39-7.73 (m, 3 H). (L26913-190)

Step 3: Preparation of 2-Fluoro-6-(trifluoromethylphenyl)-methanesulfonyl chloride Using the procedure described in Example 1, Step 3, 2-fluoro-6-(trifluoromethylphenyl)-methanesulfonic acid (15 g, 53 mmol) afforded 11 g of crude product which was purified by low-temperature crystallization from hexanes to afford 2-fluoro-6-(trifluoromethylphenyl)-methanesulfonyl chloride (9.0 g, 62%). $^1$HNMR (400 MHz, CDCl$_3$) δ 5.31 (s, 2 H), 7.38-7.51 (m, 1 H), 7.58-7.68 (m, 2 H). (L26913-192)

Example 5

PREPARATION OF 2,6-BIS(TRIFLUOROMETHYLPHENYL)-METHANESULFONYL CHLORIDE

Step 1: Preparation of 2,6-Bis(trifluoromethyl)benzoyl fluoride

Using the procedure described by W. Dmowski and K. Piasecka-Maciejewska, *Tetrahedron Lett*. 1998, 54, 6781-6792, 7.0 g of 2,6-bis(trifluoromethyl)benzoic acid was converted to the acid fluoride (7.0 g, 100%), an orange solid. $^1$HNMR (400 MHz, DMSO-d$_6$) δ 8.17 (t, J=8.0 Hz, 1 H), 8.40 (d, J=8.0 Hz, 2 H) (L27132-12, 15)

Step 2: Preparation of 2,6-Bis(trifluoromethylphenyl)benzyl alcohol

Using the procedure described by W. Dmowski and K. Piasecka-Maciejewska, *Tetrahedron Lett*. 1998, 54, 6781-6792, 7.0 g of 2,6-bis(trifluoromethyl)benzoyl fluoride was converted to the alcohol (6.6 g, 100%), a pale yellow oil. $^1$HNMR (400 MHz, CDCl$_3$) δ 4.95 (s, 2 H), 7.59 (t, J=8.0 Hz, 1 H), 7.94 (d, J=7.8 Hz, 2 H). (L27132-16)

Step 3: Preparation of 2,6-Bis(trifluoromethylphenyl)benzyl bromide

To a solution of 2,6-bis(trifluoromethylphenyl)benzyl alcohol (6.6 g, 28 mmol) and 1,3-bis(diphenylphosphino) propane (6.9 g, 17 mmol) in CH$_2$Cl$_2$ (50 mL) at 0° C. was slowly added carbon tetrabromide (11 g, 33 mmol). The mixture was stirred overnight at room temperature then added via pipette to 200 mL Et$_2$O. The mixture was filtered through Celite® and concentrated. The yellow oil was suspended in 2% EtOAc-Hex and filtered through a pad of SiO$_2$ to afford the bromide (7.2 g, 84%), a colorless oil. $^1$HNMR (400 MHz, CDCl$_3$) δ 4.78 (s, 2 H), 7.59 (t, J=7.9 Hz, 1 H), 7.92 (d, J=7.9 Hz, 2 H). (L27132-17)

Step 4: Preparation of 2,6-Bis(trifluoromethylphenyl)-methanesulfonic acid sodium salt Using the procedure described in Example 1, Step 1, 2,6-bis(trifluoromethylphenyl)benzyl bromide (7.2 g, 23 mmol) afforded 2,6-bis(trifluoromethylphenyl)-methanesulfonic acid sodium salt (3.2 g, 32%), a white solid. (L27132-19)

Step 5: Preparation of 2,6-Bis(trifluoromethylphenyl)-methanesulfonic acid

Using the procedure described in Example 1, Step 2, 2,6-bis(trifluoromethylphenyl)-methanesulfonic acid sodium salt (0.19 g, 0.44 mmol) afforded 2,6-bis(trifluoromethylphenyl)-methanesulfonic acid (0.14 g, 100%), an orange solid, which was used without further purification. $^1$HNMR (400 MHz, DMSO-d$_6$) δ 4.25 (s, 2 H), 7.64 (t, J=8.5 Hz, 1 H), 7.96 (d, J=7.8 Hz, 2 H). (L27132-21)

Step 6: Preparation of 2,6-Bis(trifluoromethylphenyl)-methanesulfonyl chloride

Using the procedure described in Example 1, Step 3, 2,6-bis(trifluoromethylphenyl)-methanesulfonic acid (0.14 g, 0.44 mmol) afforded 99 mg of crude product which was purified by low-temperature crystallization from hexanes to afford 2,6-bis(trifluoromethylphenyl)-methanesulfonyl chloride (33 mg, 23%), a white powder. $^1$HNMR (400 MHz, CDCl$_3$) δ 5.56 (s, 2 H), 7.70 (t, J=8.0 Hz, 1 H), 7.97 (d, J=8.0 Hz, 2 H). (L27132-23)

Example 6

PREPARATION OF (2-TRIFLUOROMETHYLPHENYL)-METHANESULFONYL CHLORIDE

Step 1: Preparation of (2-Trifluoromethylphenyl)-methanesulfonic acid sodium salt Using the procedure described in Example 1, Step 1, 2-(trifluoromethyl)benzyl bromide (25 g, 0.14 mol) afforded (2-trifluoromethylphenyl)-methanesulfonic acid sodium salt (22.2 g, 60%), a white solid. LC-MS showed the molecular ion of the sulfonic acid. (G9381-183)

Step 2: Preparation of (2-Trifluoromethylphenyl)-methanesulfonic acid

Using the procedure described in Example 1, Step 2, (2-trifluoromethylphenyl)-methanesulfonic acid sodium salt (22.2 g, 84 mmol) afforded (2-trifluoromethylphenyl)-methanesulfonic acid (20.3 g, ~100%), a pale yellow solid. (G9381-183)

Step 3: Preparation of (2-Trifluoromethylphenyl)-methanesulfonyl chloride

Using the procedure described in Example 1, Step 3, (2-trifluoromethylphenyl)-methanesulfonic acid (20.3 g, 84 mmol) afforded (2-trifluoromethylphenyl)-methanesulfonyl chloride (19.6 g, 90%) as a white solid after crystallization from petroleum ether. $^1$HNMR (400 MHz, CDCl$_3$) δ 5.15 (s, 2 H), 7.60 (t, J=7.6 Hz, 1 H), 7.66 (t, J=7.4 Hz, 1H), 7.80 (dd, J=7.5 & 2.8 Hz, 2 H). (G9381-184)

Example 7

PREPARATION OF (2-BENZYLOXY-PHENYL)-METHANESULFONYL CHLORIDE

Step 1: Preparation of (2-Benzyloxy-phenyl)-methanesulfonic acid

Sodium sulfite (4.2 g) was added to a stirred mixture of 1-benzyloxy-2-bromomethyl-benzene (8.9 g), tetrabutylammonium iodide (59 mg) and water (150 ml). The mixture was warmed to reflux for overnight. As the mixture cooled to 0° C., it was acidified by 6N HCl. Extraction by ethyl acetate (100 ml×6) was performed (some remained in the aqueous layer). The combined organic phases were dried over MgSO$_4$. The filtrate was concentrated in vacuo. The product was triturated by ethyl ether to give (2-benzyloxy-phenyl)-methanesulfonic acid (678 mg, 8%). $^1$H NMR (400 MHz, DMSO-D6): δ ppm 3.82 (s, 2 H) 5.09 (s, 2 H) 6.86 (t, J=7.45 Hz, 1 H) 6.96 (d, J=8.08 Hz, 1 H) 7.14 (t, J=7.83 Hz, 1 H) 7.32 (d, J=7.33 Hz, 1 H) 7.38 (t, J=7.33 Hz, 2 H) 7.46 (d, J=9.09 Hz, 1 H) 7.52 (d, J=7.07 Hz, 2 H).

Step 2: Preparation of (2-Benzyloxy-phenyl)-methanesulfonyl chloride

Tetrahydrofuran (10 ml), (2-benzyloxy-phenyl) methanesulfonic acid (138 mg), and N,N-dimethylformamide (2 drops) was cooled to −78° C. and oxalyl chloride (315 mg) was added slowly. The reaction mixture was stirred for 3 h from −78° C. to 0° C. The reaction mixture was clarified by filtration. The filtrate was washed with iced-water and heptane, and dried to give (2-benzyloxy-phenyl)-methanesulfonyl chloride (114 mg, 77%). $^1$H NMR (400 MHz, CHLOROFORM-D): δ ppm 5.06 (s, 2 H) 5.15 (s, 2 H) 7.04 (m, 2 H) 7.42 (m, 7 H).

Example 8

PREPARATION OF (2,3-DICHLOROPHENYL)-METHANESULFONYL CHLORIDE

Step 1: Preparation of (2,3-Dichlorophenyl)-methanesulfonic acid sodium salt

To a suspension of 2,3-dichlorobenzyl chloride (0.68 mL, 5.0 mmole) in 20 mL water was added sodium sulfite (630 mg, 5.0 mmole) and the mixture was heated to reflux overnight. The reaction mixture was evaporated exhaustively on the rotary evaporator and dried under vacuum to give the sodium salt of (2,3-dichlorophenyl)-methanesulfonic acid as a white solid. 1H NMR (400 MHz, DMSO-D6) δ ppm 3.97 (s, 2 H) 7.28 (t, J=7.83 Hz, 1 H) 7.49 (m, 2 H)

Step 2: Preparation of (2,3-Dichlorophenyl)-methanesulfonic acid

The sodium salt of (2,3-dichlorophenyl)-methanesulfonic acid (5.0 mmole) was suspended in 50 mL MeOH and stirred at 50° C. for 1 hour, then cooled to −10° C. HCl gas was bubbled in for several seconds and the resulting white suspension was stirred at −10° C. for 1 hour. The mixture was filtered through Celite® and evaporated. The resulting residue was triturated with 60 mL dry acetone and filtered. The filtrate was evaporated to give a yellow semi-solid. This solid was triturated with 40 mL 2:1 ether:hexane. The resulting solid was filtered and washed with hexane to give 902 mg (2,3-dichlorophenyl)-methanesulfonic acid.1H NMR (400 MHz, DMSO-D6) δ ppm 3.96 (s, 2 H) 7.27 (t, J=7.83 Hz, 1 H) 7.49 (m, 2 H)

Step 3: Preparation of (2,3-Dichlorophenyl)-methanesulfonyl chloride (2,3-dichlorophenyl)-methanesulfonic acid (260 mg, 1.0 mmole) was dissolved in 5 mL dry THF and cooled to 0° C. A catalytic drop of DMF was added followed by oxalyl chloride (0.44 mL, 5.0 mmole). The reaction mixture was allowed to warm to room temperature over 90 minutes and then filtered through Celite®, rinsing the Celite® with an additional 15 mL dry THF. The filtrate was evaporated to a volume of ca. 5 mL and then 5 mL water was added in small portions, cooling the vessel in a water bath. The mixture was extracted with 2×25 mL EtOAc and the combined organics were washed with saturated sodium bicarbonate, brine, and dried (MgSO$_4$). Filtration and evaporation gives the crude product as a yellow oil. Chromatography on silica gel using a gradient of 5% EtOAc/Hexane to 30% EtOAc/Hexane gives 142 mg (2,3-dichlorophenyl)-methanesulfonyl chloride as a white solid.1H NMR (400 MHz, CHLOROFORM-D) δ ppm 5.09 (s, 2 H) 7.25 (t, J=7.96 Hz, 1 H) 7.45 (m, 1 H) 7.53 (dd, J=8.08, 1.52 Hz, 1 H)

Example 9

PREPARATION OF (2-FORMYL-PHENYL)-METHANESULFONYL CHLORIDE

Step 1: Preparation of 2-Bromomethyl-benzaldehyde

To α-bromo-o-tolunitrile (10 g, 51 mmol) in DCM at 0° C. was added DIBAL-H (1M in hexane, 55 mL, 55 mmol) and the reaction mixture was stirred at the same temperature for 3.5 h before pouring into a solution of cold 5% HBr. After stirring for an additional 15 min, the layers were separated and the aqueous layer was extracted with DCM and the combined organic layers were washed with NaHCO$_3$ and water, dried over MgSO$_4$ and evaporated to yield a dark liquid (9.4 g). The material was used directly in the next step without further purification.

Step 2: Preparation of (2-Formyl-phenyl)-methanesulfonic acid sodium salt

Using the procedure described in Example 1, Step 1, 2-bromomethyl-benzaldehyde (1.58 g, 7.94 mol) afforded (2-formyl-phenyl)-methanesulfonic acid sodium salt (1.40 g, 80%), an off white solid. (L27234-72)

Step 3: Preparation of (2-Formyl-phenyl)-methanesulfonic acid

Using the procedure described in Example 1, Step 2, (2-formyl-phenyl)-methanesulfonic acid sodium salt (1.40 g, 6.30 mmol) afforded (2-formyl-phenyl)-methanesulfonic acid (418 mg, 33%), a pale yellow solid. (L27234-73)

Step 4: Preparation of (2-Formyl-phenyl)-methanesulfonyl chloride

Using the procedure described in Example 1, Step 3, (2-formyl-phenyl)-methanesulfonic acid (418 mg, 2.09 mmol) afforded (2-formyl-phenyl)-methanesulfonyl chloride (367 mg, 80%). $^1$HNMR (400 MHz, CDCl$_3$) δ 10.15 (s, 1 H), 7.92 (dd, 1 H), 7.74-7.61 (m, 3 H), 5.67 (s, 2 H). (L27234-74)

Example 10

PREPARATION OF (3,4-DICHLOROPHENYL)-METHANESULFONYL CHLORIDE

The title compound can be prepared by one of ordinary skill in the art with proper modification of the procedure of Example 8 such as replacing 2,3-dichlorobenzyl chloride with 3,4-dichlorobenzyl chloride as the starting material of Step 1.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention. It is intended that each of the patents, applications, and printed publications, including books, mentioned in this patent document be hereby incorporated by reference in their entirety.

What is claimed is:

1. A process for preparing a compound of Formula I:

Ar—R—SO$_2$—X     I wherein:
    Ar is aryl or heteroaryl optionally substituted by one or more substituents selected from the group consisting of halogen, C$_1$-C$_6$ alkyl, C$_3$-C$_7$ cycloalkyl, heterocycloalkyl, formyl, cyano, nitro, OH, C$_1$-C$_6$ alkoxy, arylalkyloxy, C$_1$-C$_6$ haloalkyl, C$_1$-C$_3$ perhaloalkyl, C$_1$-C$_6$ haloalkoxy, C$_1$-C$_3$ perhaloalkoxy, NR$^1$R$^2$, NR$^1$COR$^3$, aryl, aryloxy, heteroaryl and heteroaryloxy;
    R is C$_1$-C$_6$ alkylenyl;
    R$^1$ and R$^2$ are each independently selected from the group consisting of H, C$_1$-C$_6$ alkyl and C$_3$-C$_7$ cycloalkyl; or R$^1$ and R$^2$ together with the N atom to which they are attached form a 5- or 6-membered heterocycle;
    R$^3$ is selected from the group consisting of H, C$_1$-C$_6$ alkyl and C$_3$-C$_7$ cycloalkyl; and
    X is halogen;
    comprising:
    (a) reacting a compound of Formula II:

Ar—R-L     II wherein L is a leaving group, with a Group I or II metal sulfite salt optionally in the presence of a phase transfer catalyst to form a sulfonic acid salt compound of Formula III:

(Ar—R—SO$_3$$^{-1}$)$_q$M     III wherein M is a Group I or II metal ion;
    wherein q is 1 where M is Group I metal ion, and q is 2 where M is a Group II metal ion;
    (b) reacting said compound of Formula III with a protic acid to form a sulfonic acid compound of Formula IV:

Ar—R—SO$_3$H     IV and
    (c) reacting said compound of Formula IV with a halogen substitution reagent to form said compound of Formula I.

2. A process according to claim 1 wherein said reacting of step (a) is carried out in the presence of a phase transfer catalyst.

3. A process according to claim 1 wherein step (a) further comprises isolating said compound of Formula III by precipitating said compound of Formula III and optionally filtering the resulting precipitate.

4. A process according to claim 1 wherein said reacting of step (a) is carried out in a solvent comprising water.

5. A process according to claim 3 wherein said precipitating is facilitated by:
    (1) treating the reaction mixture of step (a) with a water-soluble metal halide salt; or
    (2) adding solvent that is not substantially miscible with water to the reaction mixture of step (a);
    or both (1) and (2).

6. A process according to claim 5 wherein said water-soluble metal halide salt comprises NaCl.

7. A process according to claim 5 wherein said solvent that is not substantially miscible with water comprises ethyl acetate.

8. A process according to claim 1 wherein said protic acid of step (b) is selected from the group consisting of HCl, HBr, H$_3$PO$_4$, HNO$_3$, HClO$_4$, and H$_2$SO$_4$, or a combination thereof.

9. A process according to claim 8 wherein said protic acid is HCl.

10. A process according to claim 9 wherein said protic acid is gaseous HCl.

11. A process according to claim 1 wherein said reacting of step (b) is carried out in a solvent comprising an alcohol.

12. A process according to claim 11 wherein said solvent comprises methanol.

13. A process according to claim 1 wherein said step (b) further comprises isolating said compound of Formula IV by precipitating said compound of Formula IV, and optionally filtering the resulting precipitate.

14. A process according to claim 1 wherein said halogen substitution reagent is selected from the group consisting of $SOCl_2$, $POCl_3$, $CCl_4$/triphenylphosphine, oxalyl chloride and oxalyl bromide.

15. A process according to claim 1 wherein said halogen substitution reagent comprises oxalyl chloride.

16. A process according to claim 1 wherein said reacting of step (c) is carried out in the presence of an acyl transfer catalyst.

17. A process according to claim 16 wherein said acyl transfer catalyst comprises a tertiary amide.

18. The process of claim 16 wherein said acyl transfer catalyst comprises N,N-dimethylformamide.

19. A process according to claim 1 wherein Ar is phenyl optionally substituted by one or more substituents independently selected from the group consisting of halogen, $C_1$-$C_6$ alkyl, $C_3$-$C_7$ cycloalkyl, heterocycloalkyl, formyl, cyano, nitro, OH, $C_1$-$C_6$ alkoxy, arylalkyloxy, $C_1$-$C_6$ haloalkyl, $C_1$-$C_3$ perhaloalkyl, $C_1$-$C_6$ haloalkoxy, $C_1$-$C_3$ perhaloalkoxy, $NR^1R^2$, $NR^1COR^3$, aryl, aryloxy, heteroaryl, and heteroaryloxy.

20. A process according to claim 19 wherein Ar is phenyl substituted by one or more substituents selected from the group consisting of halogen, $C_1$-$C_6$ alkyl, $C_1$-$C_3$ perhaloalkyl, formyl, and arylalkyloxy.

21. A process according to claim 1 wherein R is $C_1$-$C_4$ alkylene.

22. A process according to claim 21 wherein R is methylene.

23. A process according to claim 1 wherein L is selected from the group consisting of halogen, $OSO_2CH_3$, $OSO_2CF_3$, and $OSO_2$-aryl' wherein aryl' is a phenyl group optionally substituted with 1, 2 or 3 substituents independently selected from the group consisting of $C_1$-$C_3$ alkyl and halogen.

24. A process according to claim 23 wherein L is Cl.

25. A process according to claim 1 wherein M is $Na^+$ ion or $K^+$ ion.

26. A process according to claim 1 wherein X is Cl.

27. A process according to claim 1 wherein:

Ar is phenyl optionally substituents by one or more substituent selected from the group consisting of halogen, $C_1$-$C_6$ alkyl, $C_1$-$C_3$ perhaloalkyl, formyl, arylalkyloxy, $NR^1R^2$ and $NR^1COR^3$;

R is methylene or ethylene;

$R^1$ and $R^2$ are each, independently, H or $C_1$-$C_6$ alkyl;

$R^3$ is H or $C_1$-$C_6$ alkyl;

X is Cl;

L is halogen;

said metal sulfite salt of step (a) is $Na_2SO_3$;

said phase transfer catalyst of step (a) is present;

said sulfonic acid salt compound of Formula III has the Formula $NaSO_3$—R—Ar;

said step (a) further comprises isolating said compound of Formula III;

said step (b) further comprises isolating said compound of Formula IV; and said halogen substitution reagent of step (c) is oxalyl chloride.

28. A process according to claim 1 wherein the compound of Formula I is (3,4-dichlorophenyl)-methanesulfonyl chloride, (2,6-dimethylpheny)-methanesulfonyl chloride, (2-methylphenyl)-methanesulfonyl chloride, (2,6-difluorophenyl)-methanesulfonyl chloride, 2-fluoro-6-(trifluoromethylphenyl)-methanesulfonyl chloride, 2,6-Bis(trifluoromethylphenyl)-methanesulfonyl chloride, (2-trifluoromethylphenyl)-methanesulfonyl chloride, (2-benzyloxy-phenyl)-methanesulfonyl chloride, (2,3-dichlorophenyl)-methanesulfonyl chloride, or (2-formylphenyl)-methanesulfonyl chloride.

29. A process according to claim 1 wherein the compound of Formula I, Ar, R and X are selected in accordance with the table hereinbelow:

| Ar | R | X | Compound of Formula I |
|---|---|---|---|
| 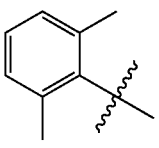 | 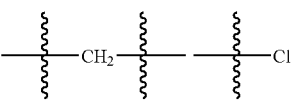 —CH$_2$— | —Cl | 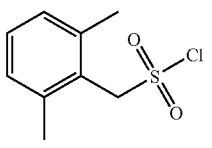 |
| 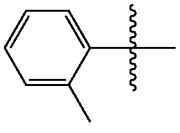 | 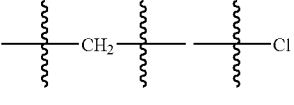 —CH$_2$— | —Cl | 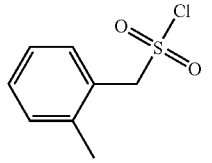 |

-continued
| Ar | R | X | Compound of Formula I |
|---|---|---|---|
| 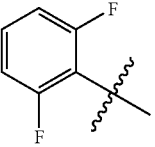 | 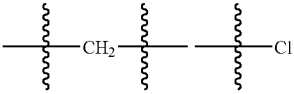 —CH₂— | 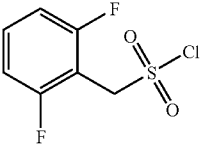 —Cl | 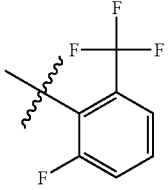 |
| 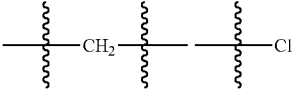 | 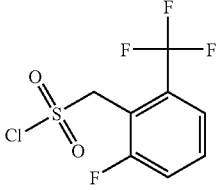 —CH₂— | —Cl | 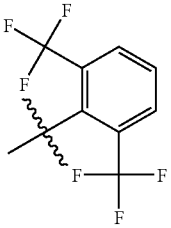 |
| 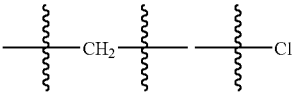 | 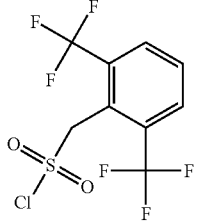 —CH₂— | —Cl | 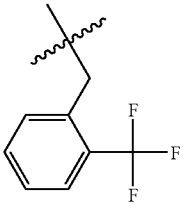 |
| 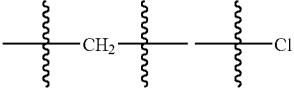 | 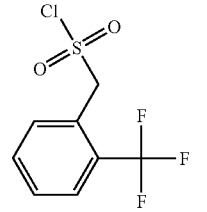 —CH₂— | —Cl | 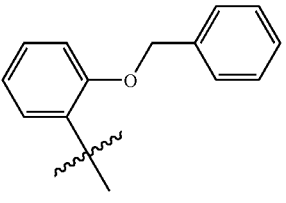 |
| 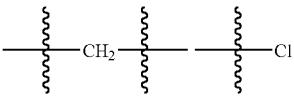 | 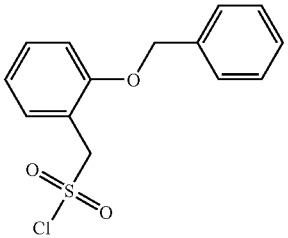 —CH₂— | —Cl | 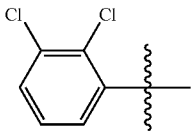 |
| 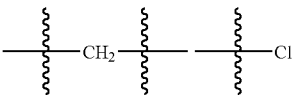 | 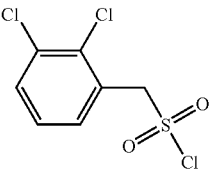 —CH₂— | —Cl | 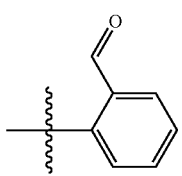 |
| 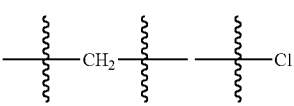 | —CH₂— | —Cl | 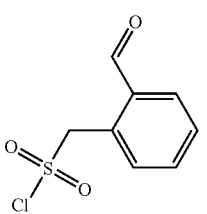 |

| Ar | R | X | Compound of Formula I |
|---|---|---|---|
| 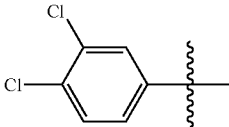 | 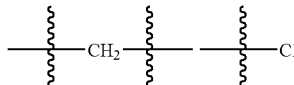—CH$_2$— | —Cl | 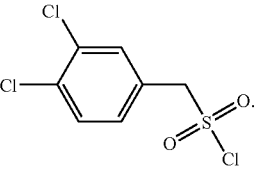 |
* * * * *